(12) United States Patent
Herrwerth et al.

(10) Patent No.: US 8,778,319 B2
(45) Date of Patent: Jul. 15, 2014

(54) POLYSILOXANES HAVING QUATERNARY AMMONIUM GROUPS, METHOD FOR PRODUCING SAME AND USE THEREOF IN FORMULATIONS FOR CLEANSING AND CARE

(75) Inventors: Sascha Herrwerth, Essen (DE); Christian Hartung, Essen (DE); Patrick Winter, Muelheim an der Ruhr (DE); Michael Ferenz, Essen (DE); Frauke Henning, Essen (DE)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 13/522,560

(22) PCT Filed: Dec. 17, 2010

(86) PCT No.: PCT/EP2010/070071
§ 371 (c)(1),
(2), (4) Date: Jul. 17, 2012

(87) PCT Pub. No.: WO2011/088937
PCT Pub. Date: Jul. 28, 2011

(65) Prior Publication Data
US 2012/0294819 A1     Nov. 22, 2012

(30) Foreign Application Priority Data
Jan. 19, 2010  (DE) .................. 10 2010 000 993

(51) Int. Cl.
- C07F 7/10 (2006.01)
- A61K 8/58 (2006.01)
- A61Q 5/02 (2006.01)
- A61Q 5/06 (2006.01)
- A61K 8/898 (2006.01)
- A61K 47/24 (2006.01)
- A61Q 5/12 (2006.01)

(52) U.S. Cl.
USPC ....... 424/70.122; 510/122; 514/788; 556/419

(58) Field of Classification Search
None
See application file for complete search history.

(56) References Cited

U.S. PATENT DOCUMENTS

| | | |
|---|---|---|
| 4,895,964 A | 1/1990 | Margida |
| 5,152,984 A | 10/1992 | Varaprath et al. |
| 6,207,141 B1 | 3/2001 | Pyles |
| 7,083,828 B2 | 8/2006 | Mueller et al. |
| 7,196,153 B2 | 3/2007 | Burkhart et al. |
| 7,442,666 B2 | 10/2008 | Herrwerth et al. |
| 7,531,598 B2 | 5/2009 | Mueller et al. |
| 7,598,334 B2 | 10/2009 | Ferenz et al. |
| 7,605,284 B2 | 10/2009 | Brueckner et al. |
| 7,612,158 B2 | 11/2009 | Burkhart et al. |
| 7,619,035 B2 | 11/2009 | Henning et al. |
| 7,635,581 B2 | 12/2009 | Ferenz et al. |
| 7,727,599 B2 | 6/2010 | Doehler et al. |
| 7,759,402 B2 | 7/2010 | Venzmer et al. |
| 7,776,989 B2 | 8/2010 | Ferenz et al. |
| 7,825,207 B2 | 11/2010 | Ferenz et al. |
| 7,834,122 B2 | 11/2010 | Ferenz et al. |
| 7,855,265 B2 | 12/2010 | Thum et al. |
| 7,893,128 B2 | 2/2011 | Busch et al. |
| 7,964,694 B2 | 6/2011 | Ferenz et al. |
| 8,030,366 B2 | 10/2011 | Ferenz et al. |
| 8,034,173 B2 | 10/2011 | Dietz et al. |
| 8,084,633 B2 | 12/2011 | Herrwerth et al. |
| 8,138,294 B2 | 3/2012 | Henning et al. |
| 2004/0258651 A1 | 12/2004 | Pascaly et al. |
| 2005/0136269 A1 | 6/2005 | Doehler et al. |
| 2005/0139120 A1 | 6/2005 | Muller et al. |
| 2005/0255073 A1 | 11/2005 | Sockel et al. |
| 2006/0155090 A1 | 7/2006 | Ferenz |
| 2007/0059539 A1 | 3/2007 | Doehler et al. |
| 2007/0123599 A1 | 5/2007 | Eilbracht et al. |
| 2007/0197678 A1 | 8/2007 | Cavaleiro et al. |
| 2007/0299231 A1 | 12/2007 | Doehler et al. |
| 2008/0125503 A1 | 5/2008 | Henning et al. |
| 2008/0187702 A1 | 8/2008 | Ferenz et al. |
| 2008/0305065 A1 | 12/2008 | Ferenz et al. |
| 2009/0007483 A1 | 1/2009 | Hansel et al. |
| 2009/0054521 A1 | 2/2009 | Herrwerth et al. |
| 2010/0022435 A1 | 1/2010 | Henning et al. |
| 2010/0029587 A1 | 2/2010 | Brueckner et al. |
| 2010/0031852 A1 | 2/2010 | Herrwerth et al. |
| 2010/0034765 A1 | 2/2010 | Herrwerth et al. |
| 2010/0036011 A1 | 2/2010 | De Gans et al. |
| 2010/0055760 A1 | 3/2010 | Thum et al. |
| 2010/0056649 A1 | 3/2010 | Henning et al. |

(Continued)

FOREIGN PATENT DOCUMENTS

| | | |
|---|---|---|
| DE | 1493384 | 7/1965 |
| DE | 33 40 708 A1 | 5/1984 |
| DE | 37 19 086 C1 | 10/1988 |
| DE | 10327871 A1 | 1/2005 |
| DE | 102007055485 A1 | 6/2009 |

(Continued)

OTHER PUBLICATIONS

International Search Report dated Jan. 27, 2011 issued in PCT/EP2010/070071.

Schrader, K., "Grundlagen and Rezepturen der Kosmetika", 2nd edition, pp. 329 to 341, Hüthig Buch Verlag Heidelberg, 1989 (cited in English-language Specification).

English translation of a Japanese Office Action dated Feb. 6, 2014 issued in Japanese Patent Application No. 2012-548367.

*Primary Examiner* — Robert A Wax
*Assistant Examiner* — Randeep Singh
(74) *Attorney, Agent, or Firm* — Scully, Scott, Murphy & Presser, P.C.

(57) ABSTRACT

The invention relates to novel polysiloxanes having quaternary ammonium groups, and to a method for producing same. The invention further relates to the use of said polymers as an active care ingredient in formulations for the care and cleansing of skin and skin appendages, for example, as conditioning agents for hair.

6 Claims, No Drawings

(56) References Cited

U.S. PATENT DOCUMENTS

| | | |
|---|---|---|
| 2010/0056818 A1 | 3/2010 | Ferenz et al. |
| 2010/0081763 A1 | 4/2010 | Meyer et al. |
| 2010/0105843 A1 | 4/2010 | Knott et al. |
| 2010/0113633 A1 | 5/2010 | Henning et al. |
| 2010/0184913 A1 | 7/2010 | Ebbrecht et al. |
| 2010/0210445 A1 | 8/2010 | von Rymon Lipinski et al. |
| 2010/0248325 A1 | 9/2010 | Eckstein et al. |
| 2010/0249339 A1 | 9/2010 | Henning et al. |
| 2010/0266651 A1 | 10/2010 | Czech et al. |
| 2010/0298455 A1 | 11/2010 | Henning et al. |
| 2011/0021693 A1 | 1/2011 | Henning et al. |
| 2011/0034576 A1 | 2/2011 | Henning et al. |
| 2011/0042004 A1 | 2/2011 | Schubert et al. |
| 2011/0046305 A1 | 2/2011 | Schubert et al. |
| 2011/0070175 A1 | 3/2011 | Herrwerth et al. |
| 2011/0091399 A1 | 4/2011 | Meyer et al. |
| 2011/0172373 A1 | 7/2011 | Knott et al. |
| 2011/0206623 A1 | 8/2011 | Wenk et al. |
| 2011/0230619 A1 | 9/2011 | Kuppert et al. |
| 2011/0230633 A1 | 9/2011 | Ferenz et al. |
| 2011/0245412 A1 | 10/2011 | Schubert et al. |
| 2011/0251070 A1 | 10/2011 | Poffenberger et al. |
| 2011/0306694 A1 | 12/2011 | Glos et al. |
| 2012/0010302 A1 | 1/2012 | Hartung et al. |
| 2012/0021960 A1 | 1/2012 | Wenk et al. |
| 2012/0029090 A1 | 2/2012 | Brugger et al. |
| 2012/0046486 A1 | 2/2012 | Henning et al. |

FOREIGN PATENT DOCUMENTS

| | | |
|---|---|---|
| DE | 102008001788 A1 | 11/2009 |
| DE | 102008041601 A1 | 3/2010 |
| EP | 0017122 A1 | 10/1980 |
| EP | 0 294 642 A2 | 12/1988 |
| EP | 0 530 974 A1 | 3/1993 |
| EP | 0 617 607 A1 | 10/1994 |
| EP | 1 080 714 A2 | 3/2001 |
| EP | 1 520 870 A1 | 4/2005 |
| EP | 1 561 770 A1 | 8/2005 |
| EP | 1439200 B1 | 6/2007 |
| JP | H04292627 A | 10/1992 |
| JP | 2005520880 A | 7/2005 |
| JP | 2008031481 A | 2/2008 |
| JP | 2010037344 A | 2/2010 |
| WO | WO 0182879 A2 | 11/2001 |

POLYSILOXANES HAVING QUATERNARY AMMONIUM GROUPS, METHOD FOR PRODUCING SAME AND USE THEREOF IN FORMULATIONS FOR CLEANSING AND CARE

FIELD OF THE INVENTION

The invention relates to innovative polysiloxanes having quaternary ammonium groups and also to a process for preparing them. It further relates to the use of these polymers as an active care ingredient in formulations for the care and cleaning of skin and epidermal derivatives, such as, for example, as conditioning agents for hair, and also in cleaning and maintenance products in household and industry.

PRIOR ART

Polysiloxanes having quaternary ammonium groups and the application thereof as additives for haircare or textile softeners are known from the patent literature.

Thus, for example, DE 14 93 384, EP 0017122, and U.S. Pat. No. 4,895,964 describe structures in which siloxanes have been modified in middle positions with quaternary ammonium groups distributed statistically over the polymer. These compounds have the disadvantage that they do not possess a pronounced silicone character, and effective activity as conditioning agents for hair or textiles, for example, is not observed. A pronounced silicone character is possessed by cationic polysiloxanes of the kind described in DE 37 19 086 and EP 0 294 642. With the structures described in DE 37 19 086 and the structures described in EP 0 294 642, the quaternary functions are attached in terminal positions on the polysiloxane. Compounds of these kinds offer advantages in terms of their effect as conditioning agents not only for hair and textiles but also for hard surfaces. The use of such compounds in cosmetic formulations has been described in, for example, EP0530974, EP617607, EP1080714, WO2001082879, and U.S. Pat. No. 6,207,141.

Nevertheless, the structures described therein possess only two cationic groups. On account of the relatively low substantivity, the affinity of the polysiloxanes for particular surfaces is relatively small.

Known from DE-A 33 40 708 are polyquaternary polysiloxane polymers. Polyquaternary polysiloxane polymers of this type do not have the disadvantages described above. The practical use of these compounds is opposed, however, by the complex and expensive processes by which they are prepared. The compounds are preparable in economically unacceptable yields of <60% of theory.

Human hair is daily exposed to a very wide variety of influences. As well as mechanical stresses from brushing, combing, putting up or tying back, the hair is also attacked by environmental influences such as, for example, strong UV radiation, cold, wind, and water. The physiological status (e.g., age, health) of the person in question also affects the state of the keratinic fibers.

Treatment with chemical agents, in particular, alters structure and surface properties of the hair. Methods such as, for example, permanent-waving, bleaching, coloring, tinting, straightening, etc., and also frequent washing with aggressive surfactants, are among the causes of more or less severe damage to the hair structure. In the case of a permanent-wave treatment, for example, both the cortex and the cuticle of the hair are attacked. The disulfide bridges of the cystine are broken by the reducing step and partly oxidized to acid cysteine in the subsequent oxidation step.

In the case of bleaching, not only is the melanine destroyed, but also about 15% to 25% of the disulfide bonds in the cystine are oxidized in the case of a mild bleaching treatment. In the case of excessive bleaching, the figure may be even up to 45% (K. F. de Polo, A Short Textbook of Cosmetology, 2000, Verlag für chemische Industrie, H. Ziolkowsky GmbH).

Accordingly, the chemical treatments, the frequent washing or the CV irradiation produce adverse mechanical properties for the hair, induced by removal of naturally secreted hair fats or humectants (sebum), The hair, as a result, becomes brittle, dry, dull, porous, and difficult to comb.

Moreover, thoroughly cleaned hair is commonly very difficult to comb, in both the wet and dry states, since the individual hairs tend to become frizzy and to knot. The hair therefore loses its resistance initially during washing and subsequently during combing. This loss of resistance is manifested in a significant decrease in the tensile strength in wet hair. Moreover, it is less resistant than healthy hair to further damage from chemicals, surfactants, and environmental effects.

For the care of hair damaged in this way there are specific preparations, such as, for example, hair rinses, hair repair treatments, shampoos, leave-in conditioners, and so on, which are able, however, to improve in particular the combability, the feel and the sheen of damaged hair. Commercial haircare compositions of these kinds comprise primarily cationic, alkylammonium-based surfactants, polymers, waxes or oils or silicone fluids. The activity of these compounds can be attributed to effects including the hydrophobizing of the hair surface.

With all of these compositions, the care effect (conditioning) of the hair that is achieved is good, and yet the appearance, particularly the sheen of the hair, is not improved by the care products, and in some cases is even impaired.

Consequently, then, there continues to be a demand for versatile active ingredients for personal hygiene and care compositions such as shampoos, hair treatment compositions, and hair aftertreatment compositions, which as well as the cleaning effect enhance the care of the hair and at the same time impart good sheen, which protect the hair from damage to the hair structure, and which minimize the structural damage already caused to the hair through environmental effects and also shaping and coloring treatments.

It is an object of the invention to provide an active ingredient of this kind which is capable not only of enhancing properties such as combability, softness, volume, shapability, handlability, and detanglability of damaged and undamaged hair, but also of giving the hair an attractive sheen. The compounds, therefore, are to exhibit an improved or at least equally good individual effect, but overall an improved combined effect of mechanical and other properties.

DESCRIPTION OF THE INVENTION

Surprisingly it has been found that siloxanes of the general formula (I), comprising quaternary ammonium groups and being branched in the siloxane moiety, achieve the stated objects.

One advantage of the siloxanes of the invention is that they unite the advantages of sidechain-modified siloxanes and of α,ω-modified siloxanes and exhibit a higher degree of modification in the sense of a greater number of substitution possibilities in comparison to purely linear structures. As a result it is possible to access structures with a long, undisrupted siloxane backbone that are able to introduce an especially good conditioning effect into cosmetic, dermatological, and pharmaceutical formulations. Another advantage of the siloxanes of the invention is that they and the downstream products manufactured from them possess no tendency, or virtually no tendency, to gel, and can therefore be stored for a relatively long period of time without critical change in the viscosity of the products. This advantage can be emphasized specifically for products of high molecular mass. The products of the invention are therefore based in particular on organically modified siloxanes which comprise quaternary ammonium groups and are branched in the silicone moiety and which are therefore highly branched and also of relatively high molecular mass (average molar mass >3000 g/mol), these structures nevertheless being free from gelling and hence of comparatively low viscosity.

A further advantage of the invention is that the polysiloxanes with quaternary ammonium groups as per formula (I) are able to exert outstanding conditioning effects on skin and hair. As a result of this conditioning effect on the skin, a dry, brittle or rough skin state following applications of an aqueous, surfactant-containing formulation can be prevented, and a pleasant, velvety-silky skin feel obtained.

Another advantage is that the inventive use as active care ingredient contributes to enhanced initial foaming, an increased foam volume, and a better foam creaminess in the formulations.

Furthermore, the inventive use of the structures as an active care ingredient leads to improved hair sheen.

Where the present invention describes compounds, such as polysiloxanes, for example, which can have various units multiply, these units may occur in statistical distribution (random oligomer) or in ordered form (block oligomer) in these compounds. Data for the number of units in such compounds should be understood as an average value, averaged over all such compounds.

All percentages (%) indicated are percent by mass unless indicated otherwise.

All conditions such as pressure and temperature, for example, are standard conditions unless otherwise specified.

The present invention accordingly provides polysiloxanes which comprise at least one quaternary ammonium groups and are of the general formula (I)

$$M_a M'_{a1} M''_{a2} M'''_{a3} D_b D'_{b1} D''_{b2} D'''_{b3} T_c T'_{c1} Q_d \quad \text{formula (I)}$$

where
$M=(R^1{}_3SiO_{1/2})$
$M'=(R^2R^1{}_2SiO_{1/2})$
$M''=(R^3R^1{}_2SiO_{1/2})$
$M'''=(R^4R^1{}_2SiO_{1/2})$
$D=(R^1{}_2SiO_{2/2})$
$D'=(R^2R^1SiO_{2/2})$
$D''=(R^3R^1SiO_{2/2})$
$D'''=(R^4R^1SiO_{2/2})$
$T=(R^5SiO_{3/2})$
$T'=(R^2SiO_{3/2})$
$Q=(SiO_{4/2})$
$a=0$ to 32; preferably 0 to 22, more particularly 0 to 12;
$a1=0$ to 10, preferably 0 to 5, more particularly 0;
$a2=0$ to 32, preferably 0 to 22, more particularly 1 to 12;
$a3=0$ to 10; preferably 0 to 5, more particularly 0;
with the proviso that
$a+a1+a2+a3>3$, preferably $>4$;
$b=1$ to 600, preferably 10 to 500, more particularly 20 to 400;
$b1=0$ to 10, preferably 0 to 5, more particularly 0;
$b2=0$ to 80, preferably 0 to 50, more particularly 0 to 10;
$b3=0$ to 20, preferably 0 to 10, more particularly 0;
$c=0$ to 30, preferably 1 to 20, more particularly 2 to 15;
$c1=0$ to 10, preferably 0 to 5, more particularly 0;
$d=0$ to 15, preferably 1 to 12, more particularly 2 to 10;
with the proviso that
$a2+b2 \geq 1$, preferably $>3$ and
$c+c1+d>1$, preferably $>2$, more particularly $\geq 3$;

$R^1$=independently of one another identical or different linear or branched, optionally aromatic hydrocarbon radicals having 1 to 30 carbon atoms, preferably methyl or phenyl, more particularly methyl;

$R^2$=independently of one another identical or different alkoxy or acyloxy radicals, such as, for example, methoxy, ethoxy, n-propoxy or isopropoxy radicals, acetoxy, more particularly ethoxy or isopropoxy radicals;

$R^3$=independently of one another identical or different organic radicals which carry quaternary ammonium functions;

$R^4$=independently of one another identical or different organic epoxy radicals;

$R^5$=independently of one another identical or different radicals $R^1$, $R^3$ or $R^4$, preferably $R^1$, more particularly methyl, phenyl, dodecyl or hexadecyl.

Suitable epoxy radicals $R^4$ are, for example, preferably identical or different radicals selected from the group Suitable radicals $R^3$ are, for example, groups with the structure $-R^6-R^7$, in which $R^6$ radicals are preferably identical or different divalent radicals selected from the group

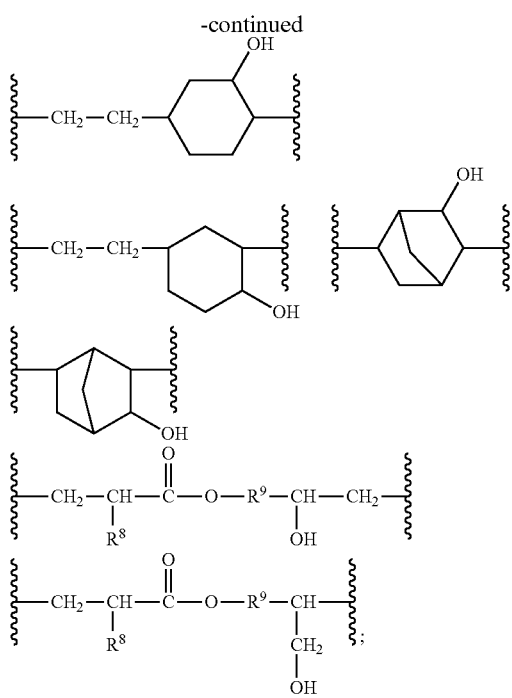

$R^6$ is preferably:

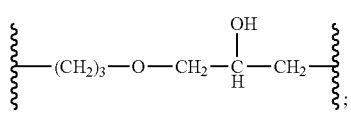

$R^7$ is selected from the group consisting of

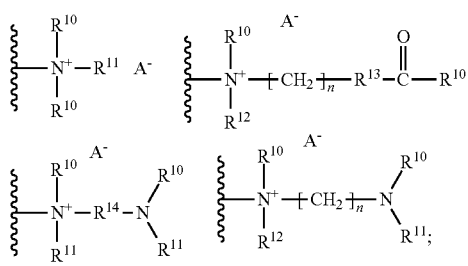

$R^8$ are identical or different radicals from the group of hydrogen or alkyl having 1 to 6 C atoms, preferably methyl;
$R^9$ are identical or different divalent hydrocarbon radicals which optionally contain ether functions, preferably methylene;
$R^{10}$, $R^{11}$, and $R^{12}$ are in each case independently of one another hydrogen or alkyl radicals having 1 to 30 C atoms, or radicals of the formula

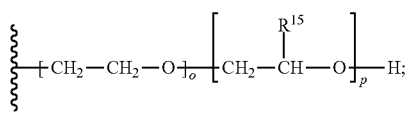

$R^{13}$ are identical or different radicals from the group —O—; —NR$^{16}$—;

$R^{14}$ are identical or different optionally branched divalent hydrocarbon radicals, preferably ethylene or propylene;
$R^{15}$ are identical or different alkyl, aryl or alkaryl radicals having 1 to 30 C atoms, which optionally contain ether functions, preferably methyl, ethyl or phenyl, more particularly methyl;
$R^{16}$ are identical or different radicals from the group of hydrogen or alkyl having 1 to 6 C atoms;
m=2 to 18;
n=2 to 18, preferably 3;
o=0 to 30, preferably 0 to 10, more particularly 1 to 3;
p=0 to 30, preferably 0 to 10;
$A^-$ are identical or different counterions to the positive charges on the quaternized nitrogen groups, selected from inorganic or organic anions of the acids HA, and also derivatives thereof.

In a further preferred embodiment of the present invention, the counterion $A^-$ to the positive charges on the quaternized nitrogen groups consists of the anion of a physiologically tolerated acid HA, which with particular preference is selected from acetic acid, L-hydroxy-carboxylic acids, more particularly lactic acid, or aromatic carboxylic acids.

Other preferred counterions come from common quaternizing agents. These are more particularly ethylsulfate, methylsulfate, toluenesulfonate, chloride, and bromide.

To the skilled person it is a familiar concept that the compounds in the form of a mixture are present with a distribution governed essentially by laws of statistics.

Preparation of the Siloxanes of the Invention

The present invention further provides a process for preparing the polysiloxanes of the general formula (I) according to the invention, comprising the steps of
A) preparing an SiH-group-containing siloxane framework, branched via at least two units selected from T and Q units, by equilibration and condensation of a mixture comprising the components
a) at least one SiH-functional siloxane,
b) at least one SiH-function-free siloxane, and either component c) or component d), or both components c) and d), where
c) is at least one tetraalkoxysilane,
d) is at least one trialkoxysilane with addition of water and at least one suitable catalyst,
B) hydrosilylating the Sili-functional siloxanes from process step A) with at least one unsaturated epoxide,
C) quaternizing the epoxysiloxanes from process step B) with at least one tertiary amine.

It is preferred in accordance with the invention for the catalyst used in step A) of the process to be a solid catalyst, preferably a solid, Brønsted-acidic catalyst. As acid ion exchangers it is possible to use the ion exchangers known from the prior art. In step A) of the process of the invention it is possible to use not only natural ion exchangers, such as, for example, zeolites, montmorillonites, attapulgites, bentonites, and other aluminum silicates, but also synthetic ion exchangers. The latter are preferably solids (usually in grain form) having a three-dimensional, water-insoluble, high molecular mass matrix based on phenol-formaldehyde resins, or are copolymers of styrene-divinylbenzene into which numerous "anchor groups" of various acidities are incorporated. In process step A) it is possible more particualrly to use acidic aluminas or acidic ion exchange resins, such as, for example, the products known under the brand names Amberlite®, Amberlyst® or Dowex®, and Lewatit®. As acidic ion exchanger it is particularly preferred to use a sulfonic-acid ion exchange resin.

Acidic ion exchangers used in step A) of the process of the invention are preferably those of the kind described in EP 1 439 200.

It may be advantageous if in step A) of the process of the invention the catalyst used comprises at least one solid acidic ion exchanger (catalyst 1) and at least one other, nonsolid Brønsted-acidic catalyst (catalyst 2), more particularly a liquid acid. As catalyst 2 it is possible here to use a mineral acid, preferably sulfuric acid, and/or, preferably, an organic sulfonic acid, preferably trifluoromethanesulfonic acid. This catalyst mixture is preferably added directly to the reaction mixture. As catalyst it is preferred to use a mixture of trifluoromethanesulfonic acid and a sulfonic-acid ion exchange resin, preferably Lewatit® K 2621 (Bayer Material Science). The catalyst mixture preferably has a mass ratio of catalyst 1 to catalyst 2 of 10:1 to 100:1. This mass ratio is preferred more particularly for the use of a Lewatit® catalyst as catalyst 1 and of trifluoromethanesulfonic acid as catalyst 2.

Where the two catalysts 1 and 2 are used as catalyst in step A) of the process, it may be advantageous if the catalyst 2 is added first of all, preferably completely, to the mixture of starting materials, then the water is added, and the catalyst 1 is added only after the preferably complete addition of water. Alternatively, the catalysts 1 and 2 may both be added to the starting materials before the water is added.

Suitable and preferred conditions for process step A) are described in particular in patent applications DE 102008041601.0 and DE 102007055485.2, which therefore are considered in their entirety to form part of the disclosure content of this application.

In process step A) it is possible, depending on the nature of the process, for residual alkoxy groups (after partially incomplete condensation) to be present in the SiH functional siloxane. This may be achieved, for example, by discontinuing the reaction before the complete conversion is achieved in the hydrolysis and condensation reaction, or by using the water that is needed for hydrolysis in substoichiometric portions, so that not all of the alkoxy groups of the alkoxysilanes can be reacted.

Process step B) is carried out preferably in the presence of a noble metal catalyst, more particularly Pt, Rh or Ru catalysts.

Unsaturated epoxides used preferably in step of the process are, for example, allyl glycidyl ether, vinylcyclohexene oxide, norbornadiene monoepoxide. Suitable and preferred conditions for the hydrosilylation reaction in process step B) are described in particular in EP 1520870, for example; that patent is hereby introduced by reference and considered to be part of the disclosure content of the present invention.

In process step B) it is possible for some of the SiH groups not to be consumed by reaction in an SiC linking reaction, but instead to be linked to the siloxane by reaction of SiOC-attached alkoxy or acyloxy groups on the hydroxyl function. Through a suitable choice of the reaction conditions (including of the catalyst/cocatalyst, reaction temperature, sequence of addition of reactants, use of solvents), this secondary reaction can usually be sufficiently suppressed.

The epoxysiloxanes obtained in process step B) can lastly, in process step C), be reacted with tertiary amines to form the desired siloxanes which carry quaternary ammonium groups. Suitable and preferred conditions for process step C) are described in DE 37 19 086 and EP 0 294 642, for example.

The skilled person is aware that as part of a reaction sequence of this kind it is likely that secondary reactions will occur, both with regard to the equilibration of the SiH-functional siloxanes (process step A) and with regard to the hydrolysilylation (process step B) and the quaternization (process step C). The extent of the secondary reactions is dependent on factors including the nature of the reactants and the reaction conditions. Thus, for example, for the reaction of epoxysiloxanes with tertiary amines in the presence of carboxylic acids by commonplace methods, the degree of quaternization is approximately 80% to 95%.

To the skilled person it is obvious that the process of the invention will lead to mixtures of polysiloxanes, more particularly to technical mixtures. Such mixtures should be understood to be included in the term "compound of the general formula (I) prepared in accordance with the process of the invention" or "siloxane prepared in accordance with the process of the invention" as used in connection with the invention.

Use of the Products of the Invention

Additionally provided by this invention is the use of the polysiloxane of the invention or of a polysiloxane obtainable, preferably obtained, by the process of the invention for producing cosmetic, pharmaceutical or dermatological compositions.

In accordance with the invention it is possible to use water-soluble or water-insoluble polysiloxanes—this also applies in respect of the inventive uses specified below. Depending on the formulation to be produced (turbid or clear formulations), the skilled person is familiar with whether he or she should use water-soluble or insoluble polysiloxanes for producing the formulation. The term "water-insoluble" in the sense of the present invention is defined as a solubility of less than 0.01 percent by weight in aqueous solution at 20° C. and 1 bar pressure. The term "water-soluble" in the sense of the present invention is defined as a solubility of greater than or equal to 0.01 percent by weight in aqueous solution at 20° C. and 1 bar pressure.

Additionally provided by this invention is the use of the polysiloxane of the invention, or of a polysiloxane obtainable, preferably obtained, by the process of the invention as an active care ingredient in care and cleaning formulations, preferably surfactant-containing aqueous care and cleaning formulations.

The term "active care ingredient" here means a substance which fulfills the purpose of maintaining an article in its original form, of lessening or preventing the effects of external influences (e.g., time, light, temperature, pressure, soiling, chemical reaction with other reactive compounds that come into contact with the article) such as, for example, aging, soiling, fatigue, fading, or even, indeed, of improving desired positive qualities of the article. Instances of the latter include improved hair sheen or a greater elasticity in the article in question. A preferred care formulation in this context is a sheen improving care formulation.

In this context, the care and cleaning formulations are not confined to cosmetic, pharmaceutical or dermatological compositions, but instead may be any such formulations that are used in household and industry, as for instance for the care and cleaning of surfaces of inanimate articles such as, for example, tiles, wood, glass, ceramic, linoleum, plastic, painted surfaces, leather, fabrics, fibers. Examples of such articles are window panes and window sills, shower partitions, flooring such as carpets, tiles, laminates, woodblock, cork floors, marble, stone and fine stoneware floors, household ceramics such as WCs, basins, bidets, shower trays, bath tubs, door handles, fittings, household appliances such as washing machines, dryers, dishwashers, ceramic or stainless steel sinks, furniture such as tables, chairs, shelving, storage surfaces, windows, kitchenware, tableware, and cutlery, laundry, especially that more close to the body (underwear), watercraft, vehicles, and aircraft such as cars, buses, motorboats, and sailboats, tools such as surgical instruments, vacuum cleaners, machines, pipelines, tanks, and apparatus for transport, processing, and storage in food processing. In this context, therefore, the formulations are used in cleaning and care compositions for household, industry, and institutions.

In this context, the surface to be cared for and cleaned is preferably the surface of a fiber or a textile, more particularly the surface of woven textiles, laundry, upholstery or carpets.

This invention further provides for the use of the polysiloxane of the invention or of a polysiloxane obtainable, preferably obtained, by the process of the invention as a conditioning agent for hair treatment compositions and hair aftertreatment compositions, and also as an agent for improving the hair structure.

Formulations/Compositions

Further provided by this invention are cosmetic, pharmaceutical or dermatological compositions, with more particular preference surfactant-containing aqueous care and cleaning formulations, especially hair treatment compositions and hair aftertreatment compositions to be rinsed out of or left in the hair, examples being shampoos with or without a pronounced conditioning effect, 2in1 shampoos, rinses, hair treatments, hair masks, styling aids, styling compositions, blow-waving lotions, hair-setting compositions, permanent-waving compositions, hair-smoothing compositions, and compositions for coloring the hair, comprising at least one of the polysiloxanes of the invention or one of the polysiloxanes obtainable, preferably obtained, by the process of the invention.

In the compositions of the invention the polysiloxanes of the invention are used advantageously at a concentration of 0.01 to 20 percent by mass, preferably 0.1 to 8 percent by mass, more preferably of 0.2 to 4 percent by mass.

The composition of the invention may comprise, for example, at least one additional component selected from the group of
emollients,
emulsifiers,
thickeners/viscosity regulators/stabilizers,
antioxidants,
hydrotropes (or polyols),
solids and fillers,
pearlescent additives,
active deodorant and antiperspirant ingredients,
insect repellents,
self-tanning agents,
preservatives,
conditioners,
perfumes,
dyes,
active cosmetic ingredients,
care additives,
superfatting agents,
solvents.

Substances which may be used as exemplary representatives of the individual groups are known to the skilled person and can be found in German application DE 102008001788.4, for example. This patent application is hereby introduced by reference and hence considered to be part of the disclosure content.

With regard to other optional components and also to the amounts of these components that are used, reference is made expressly to the relevant handbooks that are known to the skilled person, an example being K. Schrader, "Grundlagen and Rezepturen der Kosmetika", 2nd edition, pages 329 to 341, Hüthig Buch Verlag Heidelberg.

The amounts of each of the additions are dependent on the intended use.

Typical guideline formulas for the particular applications are known prior art and are contained for example in the brochures from the manufacturers of the respective base materials and active ingredients. These existing formulations can usually be adopted without change. As and when necessary, however, the desired modifications can be undertaken without complication by means of simple tests, for adaptation and optimization.

This invention additionally provides cleaning and care formulations for household, industrial, and institutional applications, such as, for example, disinfectants, disinfectant cleaners, foam cleaners, floor cleaners, carpet cleaners, upholstery cleaners, floorcare products, marble cleaners, woodblock floor cleaners, stone and ceramic floor cleaners, wipe care compositions, stainless steel cleaners, glass cleaners, dishwashing detergents, cleaners for plastics, sanitary cleaners, wood cleaners, leather cleaners, laundry detergents, laundry care compositions, disinfectant detergents, heavy-duty detergents, mild detergents, wool detergents, fabric softeners, and impregnating compositions, comprising at least one of the polysiloxanes of the invention or one of the polysiloxanes obtainable, preferably obtained, by the process of the invention. Cleaning and care formulations for household, industrial, and institutional applications that are preferred in this context are laundry detergents, laundry care compositions, heavy-duty detergents, mild detergents, wool detergents, fabric softeners, and impregnating compositions, more particularly fabric softeners.

Working Examples

In the examples set out below, the present invention is described by way of example for the purpose of illustrating the invention, without any intention that the invention, whose breadth of application is indicated by the overall description and the claims, should be confined to the embodiments stated in the examples. Where, in the text below, ranges, general formulae or classes of compound are specified, they are intended to encompass not only the corresponding ranges or groups of compounds that are explicitly mentioned, but also all subranges and subgroups of compounds which may be obtained by extracting individual values (ranges) or compounds. Where the present description cites documents, the intention is that their content should belong in full to the disclosure content of the present invention. Where the present invention describes compounds, such as organically modified polysiloxanes, for example, which can have different monomer units multiply, these units can occur in random distribution (random oligomer) or in ordered form (block oligomer) in these compounds. Figures for numbers of units in such compounds should be understood to refer to the statistical average value, averaged over all corresponding compounds.

Preparation of the Inventive Example Product 1

A) Equilibration of a Branched SiH-Functional Polysiloxane

In accordance with the instructions in patent applications DE 102008041601.0 and DE 102007055485.2, 22.9 g (0.11 mol) of tetraethoxysilane (>98%, available from Fluka), 366.4 g (0.99 mol) of decamethylcyclopentasiloxane (available from Gelest Inc.), and 112.6 g of an α,ω-dihydrogenopolydimethyl-siloxane having a hydrogen content (SiH) of 2.93 mol SiH/kg were charged to a four-neck flask equipped with KPG stirrer, internal thermometer, dropping funnel, and distillation bridge, at 40° C. with stirring. 0.5 g of trifluoromethanesulfonic acid (available from Sigma Aldrich) was added and the mixture was stirred for 2 hours. Subsequently a mixture of 7.9 g of deionized water and 2.0 g of ethanol was added dropwise over the course of 5 minutes with stirring, and the mixture was stirred at 40° C. for 1 hour. Following addition of 30.1 g of the predried sulfonic-acid cation exchange resin Lewatit® K 2621 (10% by weight water content determined by a method based on the Karl-Fischer method), excess water and alcohol were removed by distillation under a reduced pressure of approximately 15 mbar at 40° C. for 1 hour. After the resin had been isolated by filtration, it was neutralized with 10.0 g of sodium hydrogencarbonate and filtered again. This gave a clear, colorless liquid having a hydrogen (Sib) content of 0.0655%.

B) Preparation of an Epoxysiloxane

In a 500 ml three-neck flask equipped with KPG stirrer, dropping funnel, internal thermometer, and reflux condenser, 230.8 g (0.15 mol Sib) of the SiH-siloxane prepared as per example 1a) were reacted with 22.3 g (0.20 mol) of allyl glycidyl ether, with addition of 15 ppm of cisplatin catalyst, at 120° C. under a nitrogen atmosphere. After 2 hours, complete Sib conversion was achieved. Subsequent distillation at 120° C. and 1 mbar gave a clear, colorless liquid having an epoxy content of 0.98%.

C) Reaction to Form the Quaternary Polysiloxane

A 500 ml three-neck flask equipped with KPG stirrer, dropping funnel, internal thermometer, and reflux condenser was charged at room temperature with 27.0 g (0.095 mol) of 3-N,N-dimethylaminopropyllauramide, 5.9 g (0.098 mol) of acetic acid, and 80 ml of isopropanol, and this initial charge was stirred for 1 hour. Subsequently 155.1 g (0.095 mol epoxy) of the compound prepared as per example 1b) were added dropwise. The mixture was then stirred at 65° C. under a nitrogen atmosphere for 8 hours. The isopropanol, finally, was removed by distillation at 65° C. and 1 mbar. This gave a clear, yellowish, highly viscous liquid which is described by the following statistical formula:

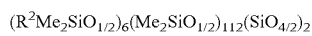

where $R^2=$

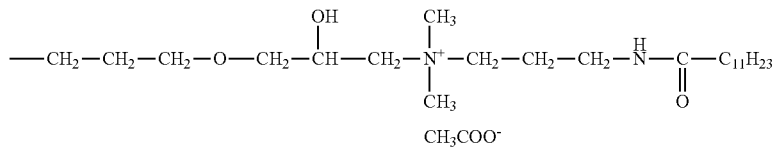

Preparation of the Inventive Example Product 2

A) Equilibration of a Branched SiH-Functional Polysiloxane

In accordance with the instructions in patent applications DE 102008041601.0 and DE 102007055485.2, 89.2 g (0.50 mol) of methyltriethoxysilane (Dynasylan® MTES from Evonik Degussa GmbH), 1023.4 g (2.76 mol) of decamethylcyclopentasiloxane (available from Gelest Inc.), and 47.0 g (0.35 mol) of 1,1,3,3-tetra-methyldisiloxane (available from Gelest Inc.) were charged to a four-neck flask equipped with KPG stirrer, internal thermometer, dropping funnel, and distillation bridge, at 40° C. with stirring. 1.2 g of trifluoromethanesulfonic acid (available from Sigma Aldrich) were added and the mixture was stirred for 2 hours. Subsequently a mixture of 27.0 g of deionized water and 6.8 g of ethanol was added dropwise over the course of 5 minutes with stirring, and the mixture was stirred at 40° C. for 1 hour. Following addition of 70.0 g of the predried sulfonic-acid cation exchange resin Lewatit® K 2621 (10% by weight water content—determined by a method based on the Karl-Fischer method), excess water and alcohol were removed by distillation under a reduced pressure of approximately 15 mbar at 40° C. for 1 hour. After the resin had been isolated by filtration, it was neutralized with 23.2 g of sodium hydrogencarbonate and filtered again. This gave a clear, colorless liquid having a hydrogen (SiH) content of 0.0634%.

B) Preparation of an Epoxysiloxane

In a 500 ml three-neck flask equipped with KPG stirrer, dropping funnel, internal thermometer, and reflux condenser, 200.0 g (0.126 mol SiH) of the SiH-siloxane prepared as per example 2a) were reacted with 18.7 g (0.164 mol) of allyl glycidyl ether, with addition of 15 ppm of cisplatin catalyst, at 120° C. under a nitrogen atmosphere. After 2 hours, complete SiH conversion was achieved. Subsequent distillation at 120° C. and 1 mbar gave a clear, colorless liquid having an epoxy content of 0.95%.

C) Reaction to Form the Quaternary Polysiloxane

A 500 ml three-neck flask equipped with KPG stirrer, dropping funnel, internal thermometer, and reflux condenser was charged at room temperature with 25.3 g (0.089 mol) of 3-N,N-dimethylaminopropyllauramide, 5.5 g (0.092 mol) of acetic acid, and 80 ml of isopropanol, and this initial charge was stirred for 1 hour. Subsequently 150.0 g (0.089 mol epoxy) of the compound prepared as per example 2b) were added dropwise. The mixture was then stirred at 65° C. under a nitrogen atmosphere for 8 hours. The isopropanol, finally, was removed by distillation at 65° C. and 1 mbar. This gave a clear, yellowish, highly viscous liquid which is described by the following statistical formula:

where $R^2=$

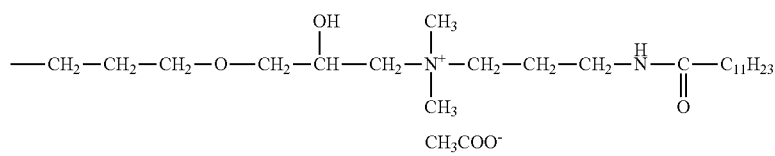

Preparation of the Comparative Example Product 3
(Not Inventive)

a) Preparation of an Epoxysiloxane

In a 1 l three-neck flask equipped with KPG stirrer, dropping funnel, internal thermometer and reflux condenser, 367 g (0.4 mol SiH) of a siloxane with conventional comblike SiH modification, of the formula $(Me_3SiO_{1/2})_2(Me_2SiO_{1/2})_{44}(MeHSiO_{1/2})_4,$ were reacted with 59 g (0.52 mol) of allyl glycidyl ether, with addition of 15 ppm of cisplatin catalyst, at 120° C. under a nitrogen atmosphere. After 2 hours, complete SiH conversion was achieved. Subsequent distillation at 120° C. and 1 mbar gave a clear, colorless liquid having an epoxy content of 1.55%.

b) Reaction to Form the Quaternary Polysiloxane

A 500 ml three-neck flask equipped with KPG stirrer, dropping funnel, internal thermometer, and reflux condenser was charged at room temperature with 28.4 g (0.10 mol) of 3-N,N-dimethylaminopropyllauramide, 6.3 g (0.105 mol) of acetic acid, and 120 ml of isopropanol, and this initial charge was stirred for 1 hour. Subsequently 206 g (0.1 mol epoxy) of the compound prepared as per example 3a) were added dropwise. The mixture was then stirred at 65° C. under a nitrogen atmosphere for 8 hours. The isopropanol, finally, was removed by distillation at 65° C. and 1 mbar. This gave a clear, yellowish, highly viscous liquid which is described by the following statistical formula:

$(Me_3SiO_{1/2})_2(Me_2SiO_{1/2})_{44}(RMeSiO_{1/2})_4$ where R=

$$-CH_2-CH_2-CH_2-O-CH_2-\underset{\phantom{X}}{\overset{OH}{CH}}-CH_2-\underset{CH_3}{\overset{CH_3}{N^+}}-CH_2-CH_2-CH_2-\overset{H}{N}-\underset{O}{\overset{\phantom{X}}{C}}-C_{11}H_{23} \quad CH_3COO^-$$

Performance Properties

The formulating ingredients are designated in the compositions in the form of the generally recognized INCI nomenclature, using the English terms. All concentrations in the application examples are given in percent by weight.

1.) Testing the Conditioning of Skin (Skincare Performance) and Foam Properties by Means of a Handwashing Test:

To evaluate the conditioning of skin (skincare performance) and the foam properties of the organically modified siloxane product 1 of the invention, with branching in the silicone moiety, in aqueous surfactant formulations, sensory handwashing tests were carried out in comparison to comparative example 3 according to the prior art.

Comparative example 3 is a widespread active care ingredient in the industry and is considered to be a highly effective active care ingredient in aqueous surfactant formulations.

A group consisting of 10 trained subjects washed their hands in a defined way and evaluated foam properties and skin feel using a grading scale from 1 (poor) to 5 (very good).

The products used were each tested in a standardized surfactant formulation (table 1).

As a control formulation 0b, a formulation without addition of an organically modified siloxane is used.

TABLE 1

Test formulations for handwashing test.

| | Formulating examples | | |
|---|---|---|---|
| | 0b | 1b | C2b |
| Texapon NSO ®, 28% form, Cognis (INCI: Sodium Laureth Sulfate) | 32% | 32% | 32% |
| TEGO Betain F 50 ®, 38% form, Evonik Goldschmidt GmbH (INCI: Cocamidopropyl Betaine) | 8% | 8% | 8% |
| NaCl | 2% | 2% | 2% |
| Water, demineralized | ad 100.0% | | |
| Product 1 (inventive) | | 0.5% | |
| Produkt 3 (not inventive) | | | 0.5% |

The sensory test results are summarized in table 2.

TABLE 2

Results of handwashing test

| Test formulation | 0b | 1b | C2b |
|---|---|---|---|
| Initial foaming | 3.0 | 3.5 | 3.3 |
| Foam volume | 2.8 | 3.2 | 2.9 |
| Foam creaminess | 2.3 | 3.3 | 3.0 |
| Skin feel during washing | 2.8 | 3.8 | 3.7 |
| Skin smoothness | 1.4 | 3.3 | 2.9 |
| Skin softness | 2.0 | 3.1 | 2.9 |
| Skin smoothness after 3 minutes | 2.6 | 3.9 | 3.6 |
| Skin softness after 3 minutes | 2.5 | 3.8 | 3.5 |

Table 2 sets out the results of the handwashing test. From the results of measurement it is clear that the inventive formulation 1b using the inventive product 1 is superior in all applications properties by comparison with the prior-art comparative formulation C2b.

In this light, the results for inventive formulation 1b can be said to be very good.

From the measurement values it is apparent that inventive product 1 in formulation 1b leads to an improvement in skin properties and foam properties as compared with product 3 in formulation C2b.

Furthermore, the measurement values indicate that the control formulation 0b without a silicone compound exhibits poorer measurement values that the formulations 1b and C2b.

2.) Testing of Hair Conditioning by Sensory Tests:

For the performance assessment of the conditioning of hair, the inventive product 2 and the comparative product 3 were used in simple cosmetic formulations (shampoo and hair rinse).

The use properties in a shampoo were verified in the following formulas:

TABLE 3

Shampoo formulations for testing the hair-conditioning properties.

| | Formulating examples | | |
|---|---|---|---|
| | 0c | 1c | C2c |
| Texapon NSO ®, 28% form, Cognis (INCI: Sodium Laureth Sulfate) | 32% | 32% | 32% |
| TEGO ® Betain F 50, 38% form, Evonik Goldschmidt GmbH (INCI: Cocamidopropyl Betaine) | 8% | 8% | 8% |
| Jaguar 162, Rhodia (INCI: Guar Hydroxypropyl trimonium Chloride) (cationic polymer for improving the activity of conditioners) | 0.3% | 0.3% | 0.3% |
| Water, demineralized | ad 100.0% | | |
| Citric acid | ad. pH 6.0 ± 0.3 | | |
| Product 2 (inventive) | | 0.5% | |
| Product 3 (not inventive) | | | 0.5% |

For the evaluation of the properties of the shampoo formulation, there was no aftertreatment with a rinse included in the test procedure.

The use properties in hair rinses were verified in the following formulas:

TABLE 4

Hair rinse formulations for testing the hair-conditioning properties.

| | Formulating examples | | |
|---|---|---|---|
| | 0d | 1d | C2d |
| TEGINACID ® C, Evonik Goldschmidt GmbH (INCI: Ceteareth-25) | 0.5% | 0.5% | 0.5% |
| TEGO ® Alkanol 16, Evonik Goldschmidt GmbH (INCI: Cetyl Alcohol) | 4% | 4% | 4% |
| VARISOFT ® 300, 30% form, Evonik Goldschmidt GmbH (INCI: Cetrimonium Chloride) | 3.3% | 3.3% | 3.3% |
| Water, demineralized | Ad 100.0% | | |
| Citric acid | ad. pH 4.0 ± 0.3 | | |
| Product 2 (inventive) | | 0.5% | |
| Product 3 (not inventive) | | | 0.5% |

When testing for the properties of hair rinses, the hair is pretreated by a shampoo containing no conditioning agents.

For the performance evaluation, hair tresses used for sensory tests are subjected to standardized preliminary damage by a permanent-waving treatment and a bleaching treatment. These treatments are carried out using standard hairdresser products. The test procedure, the base materials used and the details of the assessment criteria are described in DE 103 27 871.

Standardized treatment of ready-damaged hair strands with conditioning samples:

The hair strands subjected to preliminary damage as described above are treated as follows with the above-described shampoo or with the above-described conditioning rinse:

The hair strands are wetted under hot running water. The excess water is squeezed out easily by hand, and then the shampoo is applied and incorporated gently into the hair (1 ml/hair strand (2 g)). After a residence time of 1 minute, the hair is rinsed for 1 minute.

Directly thereafter, if desired, the rinse is applied and incorporated gently into the hair (1 ml/hair strand (2 g)). After a residence time of 1 minute, the hair is rinsed for 1 minute.

Prior to sensory assessment, the hair is dried in the air at 50% humidity and 25° C. for at least 12 hours.

Assessment Criteria:

The sensory evaluations take place according to gradings which are awarded on a scale from 1 to 5, with 1 being the poorest and 5 the best evaluation. The individual test criteria each receive a separate evaluation.

The test criteria are as follows: wet combability, wet feel, dry combability, dry feel, appearance/sheen.

In the table below, the results of sensory assessment for the treatment, carried out as described above, of the hair strands with the inventive formulation 1c, the comparative formulation C2c, and the control formulation 0c (placebo without test substance) are compared.

TABLE 5

Results of conditioning of hair from shampoo formulation

| | Wet combability | Wet feel | Dry combability | Dry feel | Sheen |
|---|---|---|---|---|---|
| Inventive formulation 1c | 3.7 | 3.5 | 3.3 | 4.3 | 4.1 |
| Comparative formulation C2c (not inventive) | 3.2 | 3.1 | 3.1 | 3.8 | 3.3 |
| Control formulation 0c (Placebo) | 2.3 | 2.5 | 2.5 | 3.3 | 2.3 |

The results show surprisingly that the inventive formulation 1c with inventive product 2 obtains significantly better evaluations than the comparative formulation C2c with the prior-art product 3. Particularly noteworthy is the good evaluation of the sheen properties of all of the inventive formulations.

TABLE 6

Results of conditioning of hair from hair rinse formulations

| | Wet combability | Wet feel | Dry combability | Dry feel | Sheen |
|---|---|---|---|---|---|
| Inventive formulation 1d | 4.9 | 4.9 | 4.7 | 4.8 | 4.5 |
| Comparative formulation C2d (not inventive) | 4.4 | 4.3 | 4.4 | 4.5 | 3.9 |
| Control formulation 0d | 3.8 | 3.9 | 4.0 | 3.8 | 2.9 |

In the hair rinse application as well, the inventive formulation 1d with inventive product 2 exhibits very good cosmetic evaluations in the sensory assessment. Here, the already very good properties of the comparative formulation C2d, with comparative product 3, were increased still further by the inventive formulation 1d, with the inventive compound 2.

A significantly better evaluation is also achieved for sheen through the use of the inventive formulation 1d.

Formulating Examples

The formulating examples below show that inventive polysiloxanes with quaternary ammonium groups can be employed in a multiplicity of cosmetic formulations.

Formulating Example 1

Clear Shampoo

| | |
|---|---|
| TEXAPON ® NSO, Cognis, 28% form (INCI: Sodium Laureth Sulfate) | 32.00% |
| Compound of example 1 | 0.50% |
| Perfume | 0.50% |
| Water | 57.50% |
| TEGO ® Betain F 50, Evonik Goldschmidt GmbH, 38% form (INCI: Cocamidopropyl Betaine) | 8.00% |
| ANTIL ® 171 Evonik Goldschmidt GmbH (INCI: PEG-18 Glyceryl Oleate/Cocoate) | 1.00% |
| NaCl | 0.50% |
| Preservative | q.s. |

Formulating Example 2

Clear Conditioning Shampoo

| | |
|---|---|
| TEXAPON ® NSO, Cognis, 28% form (INCI: Sodium Laureth Sulfate) | 32.00% |
| Compound of example 1 | 1.00% |
| Perfume | 0.50% |
| Water | 55.70% |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.30% |
| TEGO ® Betain F 50, Evonik Goldschmidt GmbH, 38% form (INCI: Cocamidopropyl Betaine) | 8.00% |
| NaCl | 1.50% |
| Preservative | q.s. |

Formulating Example 3

Clear Conditioning Shampoo

| | |
|---|---|
| TEXAPON ® NSO, Cognis, 28% form (INCI: Sodium Laureth Sulfate) | 32.00% |
| ANTIL ® 200, Evonik Goldschmidt GmbH (INCI: PEG-200 Hydrogenated Glyceryl Palmate; PEG-7 Glyceryl Cocoate) | 2.00% |
| Compound of example 2 | 1.00% |
| Perfume | 0.25% |
| Water | 56.25% |
| Polymer JR 400, Amerchol (INCI: Polyquaternium-10) | 0.20% |
| TEGO ® Betain F 50, Evonik Goldschmidt GmbH, 38% form INCI: Cocamidopropyl Betaine) | 8.00% |
| NaCl | 0.30% |
| Preservative | q.s. |

Formulating Example 4

Clear Conditioning Shampoo

| | |
|---|---|
| TEXAPON ® NSO, Cognis, 28% form (INCI: Sodium Laureth Sulfate) | 32.00% |
| ANTIL ® 200, Evonik Goldschmidt GmbH (INCI: PEG-200 Hydrogenated Glyceryl Palmate; PEG-7 Glyceryl Cocoate) | 2.00% |
| ABIL ® Quat 3272, Evonik Goldschmidt GmbH (INCI: Quaternium-80) | 0.75% |
| Compound of example 1 | 0.50% |
| Perfume | 0.25% |
| Water | 56.00% |
| Polymer JR 400, Amerchol (INCI: Polyquaternium-10) | 0.20% |
| TEGO ® Betain F 50, Evonik Goldschmidt GmbH, 38% form (INCI: Cocamidopropyl Betaine) | 8.00% |
| NaCl | 0.30% |
| Preservative | q.s. |

Formulating Example 5

Clear Conditioning Shampoo

| | |
|---|---|
| TEXAPON ® NSO, Cognis, 28% form (INCI: Sodium Laureth Sulfate) | 32.00% |
| ANTIL ® 200, Evonik Goldschmidt GmbH (INCI: PEG-200 Hydrogenated Glyceryl Palmate; PEG-7 Glyceryl Cocoate) | 2.00% |
| ABIL ® B 8832, Evonik Goldschmidt GmbH (INCI: Bis-PEG/PPG-20/20 Dimethicone) | 1.00% |
| Compound of example 1 | 0.50% |
| Perfume | 0.25% |
| Water | 55.75% |
| Polymer JR 400, Amerchol (INCI: Polyquaternium-10) | 0.20% |
| TEGO ® Betain F 50, Evonik Goldschmidt GmbH, 38% form (INCI: Cocamidopropyl Betaine) | 8.00% |
| NaCl | 0.30% |
| Preservative | q.s. |

Formulating Example 6

Clear Conditioning Shampoo

| | |
|---|---|
| TEXAPON ® NSO, Cognis, 28% form (INCI: Sodium Laureth Sulfate) | 32.00% |
| VARISOFT ® PATC, Evonik Goldschmidt GmbH (INCI: Palmitamidopropyltrimonium Chloride) | 1.50% |
| REWODERM ® LI S 80, Evonik Goldschmidt GmbH (INCI: PEG-200 Hydrogenated Glyceryl Palmate; PEG-7 Glyceryl Cocoate) | 2.00% |
| Compound of example 2 | 0.50% |
| Perfume | 0.25% |
| Water | 54.05% |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Goldschmidt GmbH, 38% form (INCI: Cocamidopropyl Betaine) | 8.00% |

Formulating example 7

Clear Conditioning Shampoo

| | |
|---|---|
| TEXAPON ® NSO, Cognis, 28% form (INCI: Sodium Laureth Sulfate) | 32.00% |
| REWODERM ® LI S 80, Evonik Goldschmidt GmbH (INCI: PEG-200 Hydrogenated Glyceryl Palmate; PEG-7 Glyceryl Cocoate) | 2.00% |
| Compound of example 2 | 0.50% |
| Perfume | 0.25% |
| Water | 55.55% |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Goldschmidt GmbH, 38% form (INCI: Cocamidopropyl Betaine) | 8.00% |
| NaCl | 0.50% |
| Preservative | q.s. |

Formulating Example 8

Pearlized Shampoo

| | |
|---|---|
| TEXAPON ® NSO, Cognis, 28% form (INCI: Sodium Laureth Sulfate) | 32.00% |
| Compound of example 1 | 0.50% |
| Perfume | 0.25% |
| Water | 55.25% |
| TEGO ® Betain F 50, Evonik Goldschmidt GmbH, 38% form (INCI: Cocamidopropyl Betaine) | 8.00% |
| TEGO ® Pearl N 300 Evonik Goldschmidt GmbH (INCI: Glycol Distearate; Laureth-4; Cocamidopropyl Betaine) | 2.00% |
| ANTIL ® 171 Evonik Goldschmidt GmbH (INCI: PEG-18 Glyceryl Oleate/Cocoate) | 1.50% |
| NaCl | 0.50% |
| Preservative | q.s. |

Formulating Example 9

2 in 1 Shampoo

| | |
|---|---|
| TEXAPON ® NSO, Cognis, 28% form (INCI: Sodium Laureth Sulfate) | 32.00% |
| VARISOFT ® PATC, Evonik Goldschmidt GmbH (INCI: Palmitamidopropyltrimonium Chloride) | 1.50% |
| REWODERM ® LI S 80, Evonik Goldschmidt GmbH (INCI: PEG-200 Hydrogenated Glyceryl Palmate; PEG-7 Glyceryl Cocoate) | 2.00% |
| Compound of example 1 | 0.50% |
| Perfume | 0.25% |
| Water | 54.05% |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Goldschmidt GmbH, 38% form (INCI: Cocamidopropyl Betaine) | 8.00% |
| NaCl | 0.50% |
| Preservative | q.s. |

Formulating Example 10

Rinse-Off Conditioner

| | |
|---|---|
| Water | 90.50% |
| VARISOFT ® BT 85, Evonik Goldschmidt GmbH (INCI: Behentrimonium Chloride) | 3.00% |
| Compound of example 1 | 1.50% |
| TEGO ® Alkanol 1618, Evonik Goldschmidt GmbH (INCI: Cetearyl Alcohol) | 5.00% |
| Preservative, Perfume | q.s. |

Formulating Example 11

Rinse-Off Conditioner

| | |
|---|---|
| Water | 90.20% |
| VARISOFT ® EQ 65, Evonik Goldschmidt GmbH (INCI: Distearyl Dimonium Chloride, Cetearyl Alcohol) | 2.00% |
| VARISOFT ® BT 85, Evonik Goldschmidt GmbH (INCI: Behentrimonium Chloride) | 2.00% |
| Compound of example 1 | 0.80% |
| TEGO ® Alkanol 1618, Evonik Goldschmidt GmbH (INCI: Cetearyl Alcohol) | 5.00% |
| Preservative, Perfume | q.s. |

Formulating Example 12

Rinse-Off Conditioner

| | |
|---|---|
| Water | 89.20% |
| VARISOFT ® EQ 65, Evonik Goldschmidt GmbH (INCI: Distearyl Dimonium Chloride, Cetearyl Alcohol) | 2.00% |
| VARISOFT ® BT 85, Evonik Goldschmidt GmbH (INCI: Behentrimonium Chloride) | 2.00% |
| ABIL ® Quat 3272, Evonik Goldschmidt GmbH (INCI: Quaternium-80) | 1.00% |
| Compound of example 1 | 0.80% |
| TEGO ® Alkanol 1618, Evonik Goldschmidt GmbH (INCI: Cetearyl Alcohol) | 5.00% |
| Preservative, Perfume | q.s. |

Formulating Example 13

Rinse-Off Conditioner

| | |
|---|---|
| TEGINACID ® C, Evonik Goldschmidt GmbH (INCI: Ceteareth-25) | 0.50% |
| TEGO ® Alkanol 16, Evonik Goldschmidt GmbH (INCI: Cetyl Alcohol) | 2.00% |
| TEGO ® Amid S 18, Evonik Goldschmidt GmbH INCI: Stearamidopropyl Dimethylamine) | 1.00% |
| Compound of example 1 | 1.50% |
| Propylene Glycol | 2.00% |
| Citric Acid Monohydrate | 0.30% |
| Water | 92.70% |
| Preservative, Perfume | q.s. |

Formulating Example 14

Rinse-Off Conditioner

| | |
|---|---|
| TEGINACID ® C, Evonik Goldschmidt GmbH (INCI: Ceteareth-25) | 0.50% |
| TEGO ® Alkanol 16, Evonik Goldschmidt GmbH (INCI: Cetyl Alcohol) | 5.00% |
| TEGOSOFT ® DEC, Evonik Goldschmidt GmbH INCI: Diethylhexyl Carbonate) | 1.00% |
| Compound of example 2 | 1.50% |
| Water | 89.20% |
| TEGO ® Cosmo C 100 Evonik Goldschmidt GmbH (INCI: Creatine) | 0.50% |
| Propylene Glycol | 2.00% |
| Citric Acid Monohydrate | 0.30% |
| Preservative, Perfume | q.s. |

Formulating Example 15

Leave-In Conditioner Spray

| | |
|---|---|
| Lactic Acid, 80% | 0.40% |
| Water | 95.30% |
| TEGO ® Amid S 18, Evonik Goldschmidt GmbH (INCI: Stearamidopropyl Dimethylamine) | 1.20% |
| TEGIN ® G 1100 Pellets, Evonik Goldschmidt GmbH (INCI: Glycol Distearate) | 0.60% |
| TEGO ® Care PS, Evonik Goldschmidt GmbH (INCI: Methyl Glucose Sesquistearate) | 1.20% |
| TEGOSOFT ® DEC, Evonik Goldschmidt GmbH (INCI: Diethylhexyl Carbonate) | 0.30% |
| Compound of example 1 | 1.00% |
| Preservative, Perfume | q.s. |

Formulating Example 16

Leave-In Conditioner Spray

| | |
|---|---|
| TAGAT ® CH-40, Evonik Goldschmidt GmbH (INCI: PEG-40 Hydrogenated Castor Oil) | 2.00% |
| Ceramide VI, Evonik Goldschmidt GmbH (INCI: Ceramide 6 II) | 0.05% |
| Perfume | 0.20% |
| Water | 90.95% |

*-continued*

| | |
|---|---|
| Compound of example 1 | 0.50% |
| LACTIL ® Evonik Goldschmidt GmbH (INCI: Sodium Lactate; Sodium PCA; Glycine; Fructose; Urea; Niacinamide; Inositol; Sodium benzoate; Lactic Acid) | 2.00% |
| TEGO ® Betain F 50 Evonik Goldschmidt GmbH 38% (INCI: Cocamidopropyl Betaine) | 2.30% |
| Citric Acid (10% in water) | 2.00% |

Formulating Example 17

Leave-In Conditioner Foam

| | |
|---|---|
| Compound of example 1 | 0.50% |
| TAGAT ® CH-40, Evonik Goldschmidt GmbH (INCI: PEG-40 Hydrogenated Castor Oil) | 0.50% |
| Perfume | 0.30% |
| TEGO ® Betain 810, Evonik Goldschmidt GmbH (INCI: Capryl/Capramidopropyl Betaine) | 2.00% |
| Water | 94.00% |
| TEGO ® Cosmo C 100, Evonik Goldschmidt GmbH (INCI: Creatine) | 0.50% |
| TEGOCEL ® HPM 50, Evonik Goldschmidt GmbH (INCI: Hydroxypropyl Methylcellulose) | 0.30% |
| VARISOFT ® 300, Evonik Goldschmidt GmbH (INCI: Cetrimonium Chloride) | 1.30% |
| LACTIL ® Evonik Goldschmidt GmbH (INCI: Sodium Lactate; Sodium PCA; Glycine; Fructose; Urea; Niacinamide; Inositol; Sodium benzoate; Lactic Acid) | 0.50% |
| Citric Acid (30% in water) | 0.10% |
| Preservative | q.s. |

Formulating Example 18

Strong Hold Styling Gel

| | |
|---|---|
| TEGO ® Carbomer 141, Evonik Goldschmidt GmbH (INCI: Carbomer) | 1.20% |
| Water | 67.00% |
| NaOH, 25% | 2.70% |
| PVP/VA W-735, ISP (INCI: PVP/VA Copolymer) | 16.00% |
| Compound of example 1 | 0.50% |
| Alcohol Denat. | 10.00% |
| TAGAT ® O 2 V, Evonik Goldschmidt GmbH (INCI: PEG-20 Glyceryl Oleate) | 2.00% |
| Perfume | 0.30% |
| ABIL ® B 88183, Evonik Goldschmidt GmbH (INCI: PEG/PPG-20/6 Dimethicone) | 0.30% |
| Preservative | q.s. |

Formulating Example 19

Body Care Foam

| | |
|---|---|
| TEXAPON ® NSO, Cognis, 28% form (INCI: Sodium Laureth Sulfate) | 14.30% |
| Perfume | 0.30% |
| Compound of example 1 | 0.50% |

-continued

| | |
|---|---|
| REWOTERIC ® AM C, Evonik Goldschmidt GmbH, 32% form (INCI: Sodium Cocoamphoacetate) | 8.00% |
| Water | 74.90% |
| TEGOCEL ® HPM 50, Evonik Goldschmidt GmbH (INCI: Hydroxypropyl Methylcellulose) | 0.50% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1.00% |
| Citric Acid Monohydrate | 0.50% |

Formulating Example 20

Body Care Composition

| | |
|---|---|
| TEXAPON ® NSO, Cognis, 28% form (INCI: Sodium Laureth Sulfate) | 30.00% |
| TEGOSOFT ® PC 31, Evonik Goldschmidt GmbH (INCI: Polyglyceryl-3 Caprate) | 0.50% |
| Compound of example 2 | 0.50% |
| Perfume | 0.30% |
| Water | 53.90% |
| TEGOCEL ® HPM 4000, Evonik Goldschmidt GmbH (INCI: Hydroxypropyl Methylcellulose) | 0.30% |
| REWOTERIC ® AM C, Evonik Goldschmidt GmbH, 32% form (INCI: Sodium Cocoamphoacetate) | 10.00% |
| Citric Acid Monohydrate | 0.50% |
| REWODERM ® LI S 80, Evonik Goldschmidt GmbH (INCI: PEG-200 Hydrogenated Glyceryl Palmate; PEG-7 Glyceryl Cocoate) | 2.00% |
| TEGO ® Pearl N 300, Evonik Goldschmidt GmbH (INCI: Glycol Distearate; Laureth-4; Cocamidopropyl Betaine) | 2.00% |

Formulating Example 21

Body Care Foam

| | |
|---|---|
| TEXAPON ® NSO, Cognis, 28% form (INCI: Sodium Laureth Sulfate) | 14.30% |
| Perfume | 0.30% |
| Compound of example 1 | 0.50% |
| REWOTERIC ® AM C, Evonik Goldschmidt GmbH, 32% form (INCI: Sodium Cocoamphoacetate) | 8.00% |
| Water | 75.10% |
| Polyquaternium-7 | 0.30% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 1.00% |
| Citric Acid Monohydrate | 0.50% |

Formulating Example 22

Mild Foam Bath

| | |
|---|---|
| TEXAPON ® NSO, Cognis, 28% form (INCI: Sodium Laureth Sulfate) | 27.00% |

-continued

| | |
|---|---|
| REWOPOL ® SB FA 30, Evonik Goldschmidt GmbH, 40% form (INCI: Disodium Laureth Sulfosuccinate) | 12.00% |
| TEGOSOFT ® LSE 65 K SOFT, Evonik Goldschmidt GmbH (INCI: Sucrose Cocoate) | 2.00% |
| Water | 39.00% |
| REWOTERIC ® AM C, Evonik Goldschmidt GmbH, 32% form (INCI: Sodium Cocoamphoacetate) | 13.00% |
| Compound of example 1 | 0.50% |
| Citric Acid (30% in water) | 3.00% |
| ANTIL ® 171 Evonik Goldschmidt GmbH (INCI: PEG-18 Glyceryl Oleate/Cocoate) | 1.50% |
| TEGO ® Pearl N 300 Evonik Goldschmidt GmbH (INCI: Glycol Distearate; Laureth-4; Cocamidopropyl Betaine) | 2.00% |

Formulating Example 23

Body Care Foam

| | |
|---|---|
| TEGOCEL ® HPM 50, Evonik Goldschmidt GmbH (INCI: Hydroxypropyl Methylcellulose) | 0.50% |
| Water | 80.10% |
| Perfume | 0.20% |
| Compound of example 1 | 0.50% |
| TEGOSOFT ® GC, Evonik Goldschmidt GmbH, (INCI: PEG-7 Glyceryl Cocoate) | 1.30% |
| TEGO ® Betain 810, Evonik Goldschmidt GmbH (INCI: Capryl/Capramidopropyl Betaine) | 16.90% |
| LACTIL ®, Evonik Goldschmidt GmbH (INCI: Sodium Lactate; Sodium PCA; Glycine; Fructose; Urea; Niacinamide; Inositol; Sodium benzoate; Lactic Acid) | 0.50% |
| Preservative | q.s. |

Formulating Example 24

Clear Shampoo

| | |
|---|---|
| TEXAPON ® NSO, Cognis, 28% form (INCI: Sodium Laureth Sulfate) | 32.00% |
| Compound of example 2 | 0.50% |
| Perfume | 0.25% |
| Water | 56.05% |
| TEGO ® Betain F 50, Evonik Goldschmidt GmbH, 38% form (INCI: Cocamidopropyl Betaine) | 8.00% |
| ANTIL ® 171 Evonik Goldschmidt GmbH (INCI: PEG-18 Glyceryl Oleate/Cocoate) | 2.50% |
| NaCl | 0.70% |
| Preservative | q.s. |

Formulating Example 25

Clear Shampoo

| | |
|---|---|
| TEXAPON ® NSO, Cognis, 28% form (INCI: Sodium Laureth Sulfate) | 32.00% |
| Compound of example 1 | 0.50% |
| Perfume | 0.25% |
| Water | 55.35% |

-continued

| | |
|---|---|
| REWOTERIC ® AMC, Evonik Goldschmidt GmbH, (INCI: Sodium Cocoamphoacetate) | 9.40% |
| ANTIL ® 171 Evonik Goldschmidt GmbH (INCI: PEG-18 Glyceryl Oleate/Cocoate) | 2.50% |
| Preservative | q.s. |

Formulating Example 25

Clear Shampoo

| | |
|---|---|
| TEXAPON ® NSO, Cognis, 28% form (INCI: Sodium Laureth Sulfate) | 17.90% |
| Compound of example 1 | 0.50% |
| Perfume | 0.25% |
| Water | 62.50% |
| TEGO ® Betain F 50, Evonik Goldschmidt GmbH, 38% form (INCI: Cocamidopropyl Betaine) | 6.60% |
| REWOPOL ® SB FA 30, Evonik Goldschmidt GmbH, (INCI: Disodium Laureth Sulfosuccinate) | 6.25% |
| ANTIL ® 171 Evonik Goldschmidt GmbH (INCI: PEG-18 Glyceryl Oleate/Cocoate) | 5.00% |
| NaCl | 1.00% |
| Preservative | q.s. |

Formulating Example 26

Rinse-Off Conditioner

| | |
|---|---|
| Water | 89.20% |
| VARISOFT ® EQ 65, Evonik Goldschmidt GmbH (INCI: Distearyl Dimonium Chloride, Cetearyl Alcohol) | 2.00% |
| VARISOFT ® BT 85, Evonik Goldschmidt GmbH (INCI: Behentrimonium Chloride) | 2.00% |
| ABIL ® OSW 5, Evonik Goldschmidt GmbH (INCI: Cyclopentasiloxane; Dimethiconol) | 1.00% |
| Compound of example 1 | 0.80% |
| TEGO ® Alkanol 1618, Evonik Goldschmidt GmbH (INCI: Cetearyl Alcohol) | 5.00% |
| Preservative, Perfume | q.s. |

Formulating Example 27

Rinse-Off Conditioner

| | |
|---|---|
| Water | 89.20% |
| VARISOFT ® EQ 65, Evonik Goldschmidt GmbH (INCI: Distearyl Dimonium Chloride, Cetearyl Alcohol) | 2.00% |
| VARISOFT ® BT 85, Evonik Goldschmidt GmbH (INCI: Behentrimonium Chloride) | 2.00% |
| ABIL ® Soft AF 100, Evonik Goldschmidt GmbH (INCI: Methoxy PEG/PPG-7/3 Aminopropyl Dimethicone) | 1.00% |
| Compound of example 1 | 0.80% |
| TEGO ® Alkanol 1618, Evonik Goldschmidt GmbH (INCI: Cetearyl Alcohol) | 5.00% |
| Preservative, Perfume | q.s. |

Formulating Example 28

Rinse-Off Conditioner

| | |
|---|---|
| Water | 89.20% |
| VARISOFT ® EQ 65, Evonik Goldschmidt GmbH (INCI: Distearyl Dimonium Chloride, Cetearyl Alcohol) | 2.00% |
| VARISOFT ® BT 85, Evonik Goldschmidt GmbH (INCI: Behentrimonium Chloride) | 2.00% |
| SF 1708, Momentive (INCI: Amodimethicone) | 1.00% |
| Compound of example 1 | 0.80% |
| TEGO ® Alkanol 1618, Evonik Goldschmidt GmbH (INCI: Cetearyl Alcohol) | 5.00% |
| Preservative, Perfume | q.s. |

Formulating Example 29

Conditioning Shampoo

| | |
|---|---|
| TEXAPON ® NSO, Cognis, 28% form (INCI: Sodium Laureth Sulfate) | 27.00% |
| Plantacare 818 UP, Cognis 51.4% form (INCI: Coco Glucoside) | 5.00% |
| Compound of example 2 | 1.50% |
| Perfume | 0.25% |
| Water | 56.55% |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Goldschmidt GmbH, 38% form (INCI: Cocamidopropyl Betaine) | 8.00% |
| NaCl | 0.50% |
| Preservative | q.s. |

Formulating Example 30

Conditioning Shampoo

| | |
|---|---|
| Plantacare 818 UP, Cognis 51.4% form (INCI: Coco Glucoside) | 18.00% |
| Compound of example 2 | 1.50% |
| Perfume | 0.25% |
| Water | 70.55% |
| TEGO ® Cosmo C 100, Evonik Goldschmidt GmbH, (INCI: Creatine) | 1.00% |
| Jaguar C-162, Rhodia (INCI: Hydroxypropyl Guar Hydroxypropyltrimonium Chloride) | 0.20% |
| TEGO ® Betain F 50, Evonik Goldschmidt GmbH, 38% form (INCI: Cocamidopropyl Betaine) | 8.00% |
| NaCl | 0.50% |
| Preservative | q.s. |

The invention claimed is:

1. A polysiloxane comprising at least one quaternary ammonium group and of the formula (I)

$$M_a M'_{a1} M''_{a2} M'''_{a3} D_b D'_{b1} D''_{b2} D'''_{b3} T_c T'_{c1} Q_d \quad \text{formula (I)},$$

wherein
$M=(R^1_3 SiO_{1/2})$
$M'=(R^2 R^1_2 SiO_{1/2})$

M''=(R³R¹₂SiO₁/₂)
M'''=(R⁴R¹₂SiO₁/₂)
D=(R¹₂SiO₂/₂)
D'=(R²R¹SiO₂/₂)
D''=(R³R¹SiO₂/₂)
D'''=(R⁴R¹SiO₂/₂)
T=(R⁵SiO₃/₂)
T'=(R²SiO₃/₂)
Q=(SiO₄/₂)
a=0 to 32,
a1=0 to 10,
a2=0 to 32,
a3=0 to 10,
with the proviso that
a+a1+a2+a3>3,
b=1 to 600,
b1=0 to 10,
b2=0 to 80,
b3=0 to 20,
c=0 to 30,
c1=0 to 10,
d=0 to 15,
with the proviso that
a2+b2≥1, and
c+c1+d≥1,
each $R^1$ is, independently of one another, an identical or different linear or branched, hydrocarbon radical having 1 to 30 carbon atoms,
each $R^2$ is, independently of one another, an identical or different alkoxy or acyloxy radical,
each $R^3$ is, independently of one another, an identical or different organic radical which has a quaternary ammonium function,
each $R^4$ is, independently of one another, an identical or different organic epoxy radical, and
each $R^5$ is, independently of one another, an identical or different radical, $R^1$, $R^3$ or $R^4$.

2. The polysiloxane as claimed in claim 1, wherein said $R^4$ radicals are identical or different radicals selected from the group consisting of:

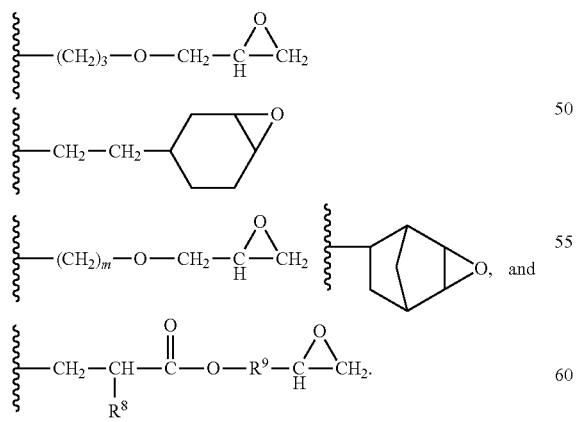

3. The polysiloxane as claimed in claim 1, wherein said $R^3$ groups are groups with the structure —$R^6$—$R^7$, wherein $R^6$ radicals are identical or different divalent radicals selected from the group consisting of

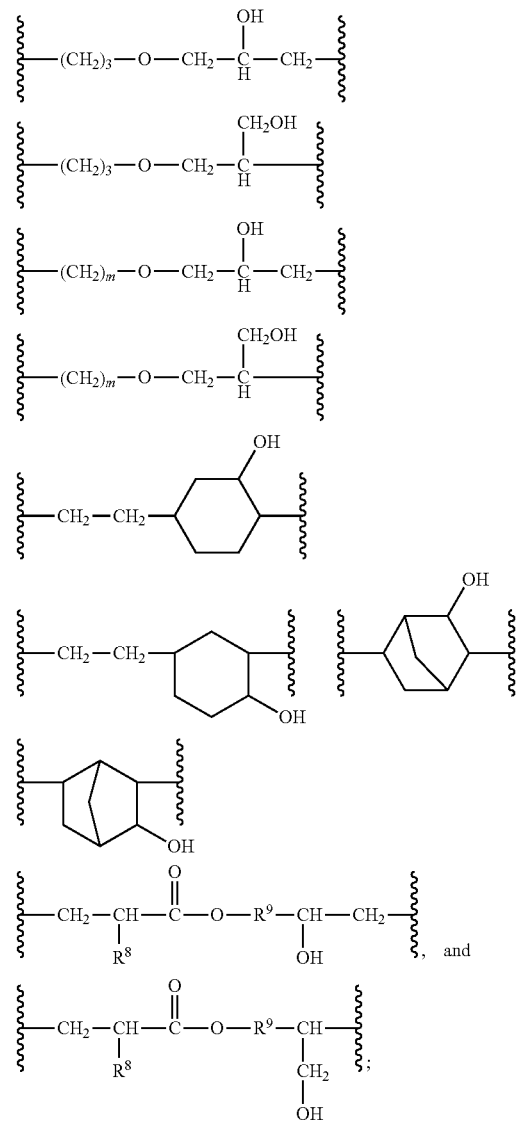

$R^7$ is selected from the group consisting of

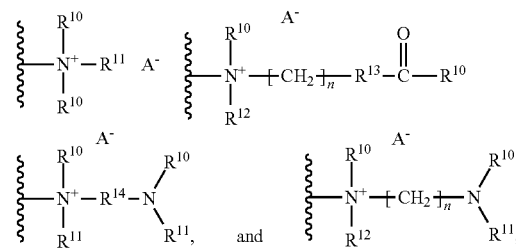

each $R^8$ is an identical or different radical and comprises hydrogen or an alkyl having 1 to 6 C atoms;

each $R^9$ is an identical or different divalent hydrocarbon radical;

$R^{10}$, $R^{11}$, and $R^{12}$ are in each case independently of one another hydrogen or alkyl radicals having 1 to 30 C atoms, or radicals of formula

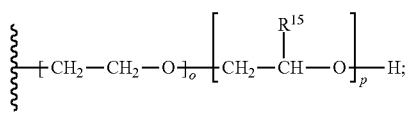

each $R^{13}$ is an identical or different radical and is —O— or —NR$^{16}$—;
each $R^{14}$ is an identical or different divalent hydrocarbon radical;
each $R^{15}$ is an identical or different alkyl, aryl or alkaryl radical having 1 to 30 C atoms;
each $R^{16}$ is an identical or different radical and is hydrogen or an alkyl having 1 to 6 C atoms;
m=2 to 18;
n=2 to 18,
o=0 to 30,
p=0 to 30,
A⁻ are identical or different counterions to positive charges on the quaternized nitrogen groups, and are inorganic or organic anions of the acids HA, or derivatives thereof.

4. A process for preparing a polysiloxane comprising:
A) preparing an SiH-group-containing siloxane framework, branched via at least two units selected from T and Q units, by equilibration and condensation of a mixture comprising the components
   a) at least one SiH-functional siloxane,
   b) at least one SiH-function-free siloxane,
   and either component c) or component d),
   or both components c) and d), where
   c) is at least one tetraalkoxysilane,
   d) is at least one trialkoxysilane
   with addition of water and at least one suitable catalyst,
B) hydrosilylating the SiH-functional siloxanes from process step A) with at least one unsaturated epoxide, and
C) quaternizing the epoxysiloxanes from process step B) with at least one tertiary amine, wherein steps a)-d) provide a polysiloxane comprising at least one quaternary ammonium group and of the formula (I)

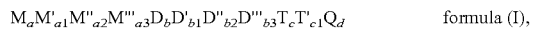

wherein
M=(R$^1$$_3$SiO$_{1/2}$)
M'=(R$^2$R$^1$$_2$SiO$_{1/2}$)
M''=(R$^3$R$^1$$_2$SiO$_{1/2}$)
M'''=(R$^4$R$^1$$_2$SiO$_{1/2}$)
D=(R$^1$$_2$SiO$_{2/2}$)
D'=(R$^2$R$^1$SiO$_{2/2}$)
D''=(R$^3$R$^1$SiO$_{2/2}$)
D'''=(R$^4$R$^1$SiO$_{2/2}$)
T=(R$^5$SiO$_{3/2}$)
T'=(R$^2$SiO$_{3/2}$)
Q=(SiO$_{4/2}$)
a=0 to 32,
a1=0 to 10,
a2=0 to 32,
a3=0 to 10,
with the proviso that
a+a1+a2+a3>3,
b=1 to 600,
b1=0 to 10,
b2=0 to 80,
b3=0 to 20,
c=0 to 30,
c1=0 to 10,
d=0 to 15,
with the proviso that
a2+b2>1, and
c+c1+d>1,
each $R^1$ is, independently of one another, an identical or different linear or branched hydrocarbon radical having 1 to 30 carbon atoms,
each $R^2$ is, independently of one another, an identical or different alkoxy or acyloxy radical,
each $R^3$ is, independently of one another, an identical or different organic radical which has a quaternary ammonium function,
each $R^4$ is, independently of one another, an identical or different organic epoxy radical, and
each $R^5$ is, independently of one another, an identical or different radical, $R^1$, $R^3$ or $R^4$.

5. A composition comprising:
at least one polysiloxane of claim 1, and a cosmetic active ingredient, a pharmaceutical active ingredient, or a dermatological active ingredient.

6. A formulation comprising at least one polysiloxane according to claim 1, and at least one additional ingredient, said at least one additional ingredient comprising an emollient, an emulsifier, a thickener/viscosity regulator/stabilizer, an antioxidant, a hydrotrope, a solid, a filler, a pearlescent additive, an active deodorant ingredient, an antiperspirant ingredient, an insect repellant, a self-tanning agent, a preservative, a conditioner, a perfume, a dye, an active cosmetic ingredient, a care additive, a superfatting agent, or a solvent.

* * * * *